(12) United States Patent
Delon et al.

(10) Patent No.: US 9,645,084 B2
(45) Date of Patent: May 9, 2017

(54) ADAPTIVE OPTICS SYSTEM

(71) Applicant: UNIVERSITE JOSEPH FOURIER, Grenoble (FR)

(72) Inventors: Antoine Delon, Corenc (FR); Charles-Edouard Leroux, Grenoble (FR); Alexei Grichine, St. Egreve (FR)

( * ) Notice: Subject to any disclaimer, the term of this patent is extended or adjusted under 35 U.S.C. 154(b) by 954 days.

(21) Appl. No.: 13/838,431

(22) Filed: Mar. 15, 2013

(65) Prior Publication Data
US 2014/0172324 A1 Jun. 19, 2014

Related U.S. Application Data

(60) Provisional application No. 61/737,427, filed on Dec. 14, 2012.

(51) Int. Cl.
*G01N 21/64* (2006.01)

(52) U.S. Cl.
CPC .............................. *G01N 21/6458* (2013.01)

(58) Field of Classification Search
CPC ............... G01N 21/6458; G01N 21/25; G01N 21/6452; G01N 2021/6419; G01N 2021/6421; G01N 15/1432; G01N 15/1456; G01N 15/1459; G01N 2015/1447; G01N 2015/145; G01N 2015/1454; G01N 2015/1486; G01J 3/44; G01J 3/4406; G01J 2003/4424; G01J 2003/2866
See application file for complete search history.

(56) References Cited

U.S. PATENT DOCUMENTS

2009/0237501 A1* 9/2009 Lemmer ............ G01N 21/6428
348/79
2014/0107944 A1* 4/2014 Ben-Amotz ........... G01N 21/65
702/30

OTHER PUBLICATIONS

M. A. Digman and E. Gratton, "Lessons in fluctuation correlation spectroscopy," Annu. Rev. Phys. Chem. 62, 645-668 (2011).
E. Haustein and P. Schwille, "Fluorescence correlation spectroscopy: novel variations of an established technique," Annu. Rev. Biophys. Biomol. Struct. 36, 151-169 (2007).
E. L. Elson, "Quick tour of fluorescence correlation spectroscopy," J. Biomed. Opt. 9,857-864 (2004).
S. T. Hess and W.W.Webb, "Focal volume optics and experimental artifacts in confocal fluorescence correlation spectroscopy," Biophys J. 83,2300-2317 (2002).
J. D. Müller, "Cumulant analysis in fluorescence fluctuation spectroscopy," Biophys. J. 86, 3981-3992 (2004).
(Continued)

*Primary Examiner* — Manuel L Barbee
(74) *Attorney, Agent, or Firm* — Howard IP Law Group, PC

(57) ABSTRACT

A disclosed method involves: receiving, by a processing device, a first plurality of photon count values indicating a number of photons detected by an optical system during a plurality of first time periods as a result of laser beam excitation of an observation volume of a sample during fluorescence fluctuation microscopy analysis; calculating, by the processing device based on the first plurality of photon count values, a first count rate per molecule indicating the average number of photons detected per molecule of the observation volume; and generating, by the processing device based on the first count rate per molecule, a control signal for configuring a phase modulation device of the optical system.

14 Claims, 2 Drawing Sheets

(56) References Cited

OTHER PUBLICATIONS

B. Huang, T. D. Perroud, and R. N. Zare, "Photon counting histogram: one-photon excitation," ChemPhysChem 5, 1523-1531 (2004).

S. Rüttinger, V. Buschmann, B. Krämer, R. Erdmann, R. Macdonald, and F, Koberling, "Comparison and accuracy of methods to determine the confocal volume for quantitative fluorescence correlation spectroscopy," J. Microsc. 232, 343-352 (2008).

T. Dertinger, A. Loman, B. Ewers, C. Müller, B. Kr amer, and J. Enderlein, "The optics and performance of dual-focus fluorescence correlation spectroscopy," Opt. Express 16, 14353-14368 (2008).

C. B. M uller, T. Eckert, A. Loman, J, Enderlein, and W. Richtering, "Dual-focus fluorescence correlation spectroscopy: a robust tool for studying molecular crowding," Soft Matter 5, 1358-1366 (2009).

N. Dross, C. Spriet, M. Zwerger, G. Müller, W, Waldeck, and J. Langowski, "Mapping eGFP oligomer mobility in living cell nuclei," PLoS ONE 4, e5041 1-13 (2009).

P. Ferrand, M. Pianta, A. Kress, A. Aillaud, and H. Rigneault, "A versatile dual spot laser scanning confocal microscopy system for advanced fuorescence correlation spectroscopy analysis in living cell," Rev. Sci. Instrum. 80, 083702 (2009).

J. Widengren, U. Mets, and R. Rigler, "Fluorescence correlation spectroscopy of triplet states in solution: a theoretical and experimental study," J. Phys. Chem. 99, 13368-13379 (1995).

J. Mertz, "Molecular photodynamics involved in multi-photon excitation fluorescence microscopy," Eur. Phys. J. D 3, 53-66 (1998).

M. Schwertner, M. Booth, and T. Wilson, "Characterizing specimen induced aberrations for high NA adaptive optical microscopy," Opt. Express 12, 6540-6552 (2004).

M. Booth, A. Kubasik-Thayil, A. Jesacher, D. D'ebarre, K. Grieve, and T.Wilson, "Adaptive optics in biomedical microscopy," in Novel Techniques in Microscopy, OSA Technical Digest (CD) (Optical Society of America, 2009), paper NWA1.

O. Azucena, J. Crest, J. Cao, W. Sullivan, P. Kner, D. Gavel, D. Dillon, S. Olivier, and J. Kubby, "Wavefront aberration measurements and corrections through thick tissue using fluorescent microsphere reference beacons," Opt. Express 18, 17521-17532 (2010).

O. Azucena, J. Crest, S. Kotadia, W. Sullivan, X. Tao, M. Reinig, D. Gavel, S. Olivier, and J. Kubby, "Adaptive optics wide-field microscopy using direct wavefront sensing," Opt. Lett. 36, 825-827 (2011).

X. Tao, B. Fernandez, O. Azucena, M. Fu, D. Garcia, Y. Zuo, D. Chen, and J. Kubby, "Adaptive optics confocal microscopy using direct wavefront sensing," Opt. Lett. 36, 1062-1064 (2011).

X. Tao, O. Azucena, M. Fu, Y. Zuo, D. Chen, and J. Kubby, "Adaptive optics microscopy with direct wavefront sensing using fluorescent protein guide stars," Opt. Lett. 36, 3389-3391 (2011).

M. Neil, M. Booth, and T. Wilson, "Closed-loop aberration correction by use of modal Zernike wave-front sensor," Opt. Lett. 25, 1083-1085 (2000).

M. Booth, M. Neil, and T. Wilson, "New modal wave-front sensor: application to adaptive confocal fluorescence microscopy and two-photon excitation fluorescence microscopy," J. Opt. Soc. Am. A 19. 2112-2120 (2002).

N. E. Dorsey, Properties of Ordinary Water-Substance in All Its Phases (New York, Reinhold Pub. Corp., 1940), p. 184.

D. R. Lide, ed., Handbook of Chemistry and Physics (CRC Press, Cleveland, 2006).

P. Kapusta, "Absolute diffusion coefficients: compilation of reference data for FCS calibration," http://www.picoquant.com/technotes/appnote diffusion coeffidents.pdf.

M. Booth, M. Neil, and T. Wilson, "Aberration correction for confocal imaging in refractive-index-mismatched media," J. Microsc. 192, 90-98 (1998).

\* cited by examiner

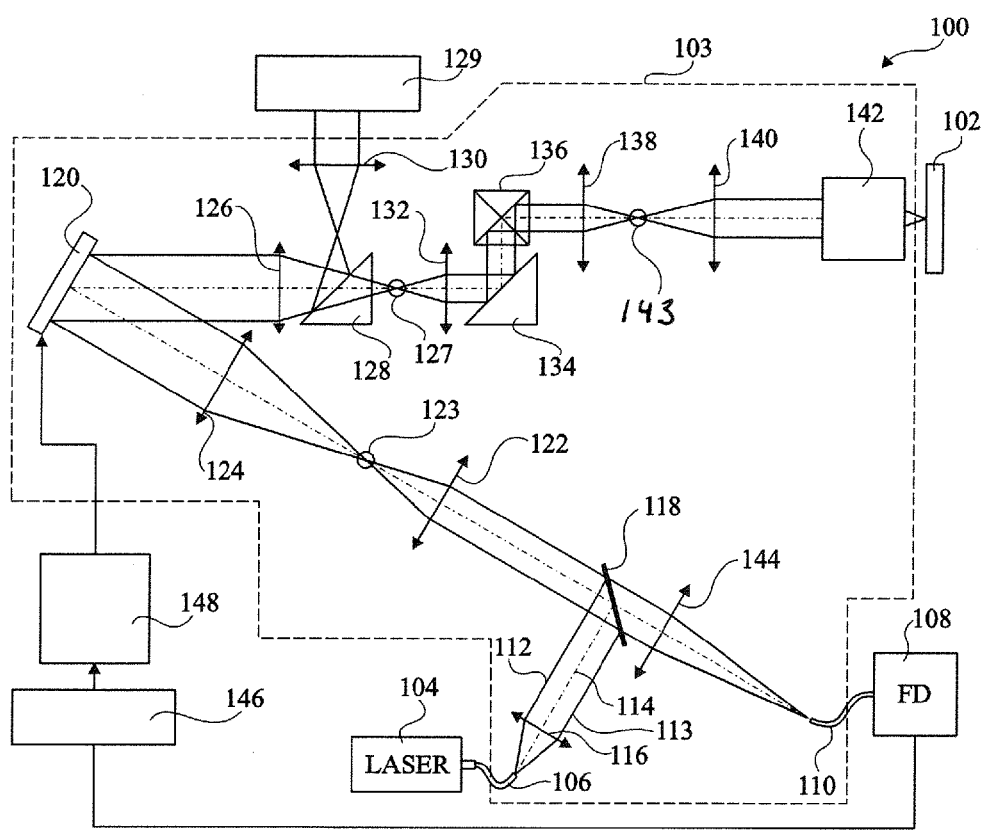
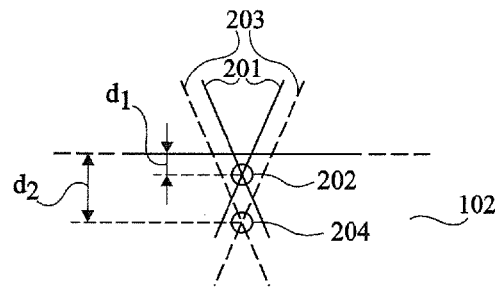
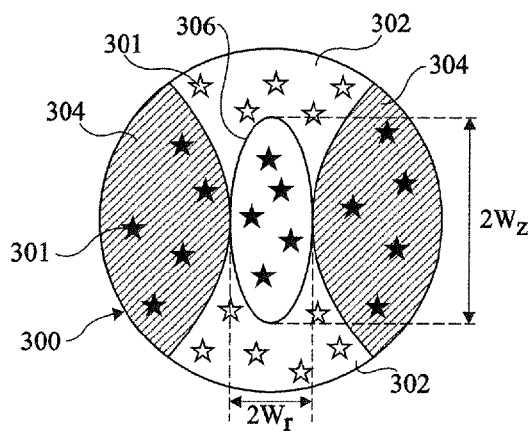
Fig 1
Fig 2
Fig 3

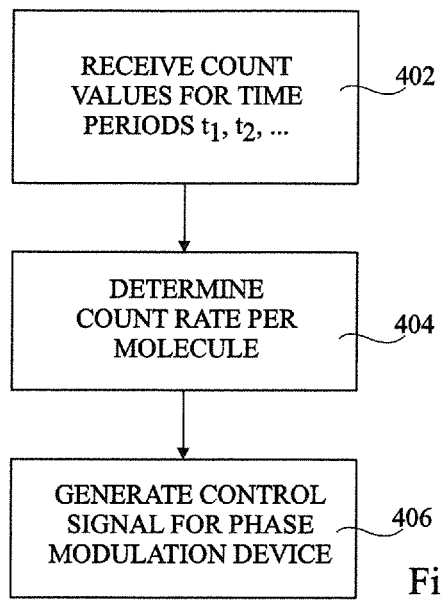
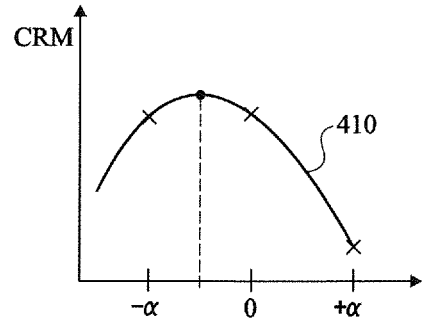
Fig 4A
Fig 4B
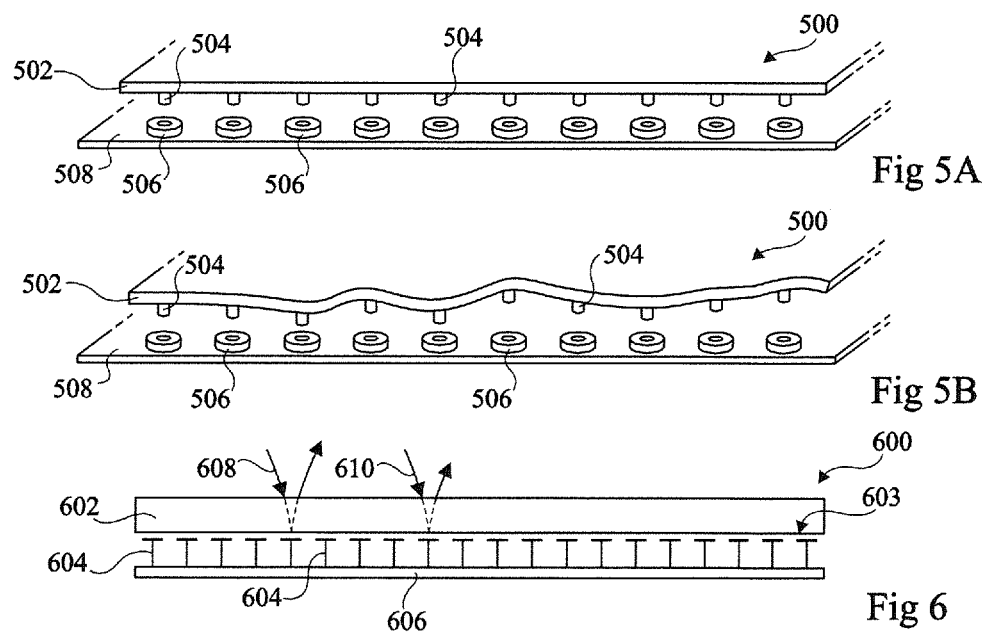
Fig 5A
Fig 5B
Fig 6
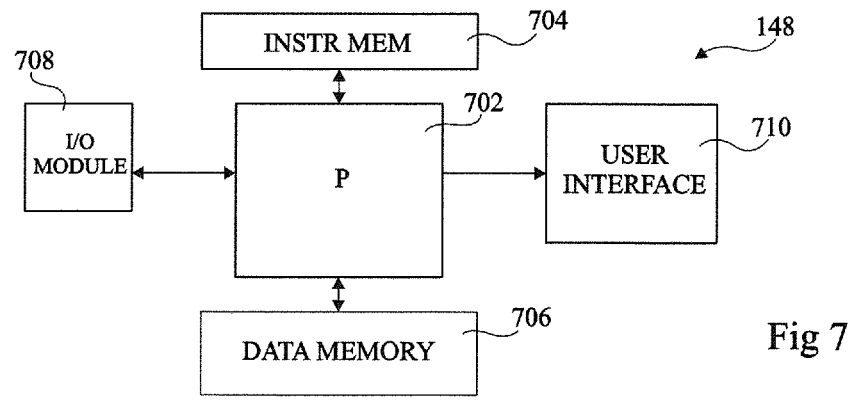
Fig 7

ADAPTIVE OPTICS SYSTEM

REFERENCE TO RELATED APPLICATION

The present application claims priority to and benefit of under 35 U.S.C. 119(e), U.S. Provisional Patent Application Ser. No. 61/737,427, filed Dec. 14, 2012, the entirety of which is incorporated herein by reference for all purposes.

FIELD

The present disclosure relates to a device, system and method for reducing optical aberrations in an optical microscope, and in particular an adaptive optics system for performing fluorescence fluctuation microscopy (FFM).

BACKGROUND

In the field of fluorescence fluctuation microscopy (FFM), fluorescence or phosphorescence from a sample can be used to study properties of organic or inorganic substances. For example, the substance to be tested contains fluorescence-tagged molecules, and it is illuminated with laser light of a wavelength chosen to excite the fluorescence. The fluorescence generated by the sample is detected, by means of an optics system comprising a suitable detector. Measurements can then be made of the sample in order to permit the quantification of molecular dynamics and molecular concentration within the sample. For example, quantities such as the mean number of molecules <N> within the observation volume, and/or the diffusion time $\tau_D$ of the molecules, can be estimated.

Fluorescence correlation spectroscopy (FCS) is a particular example of FFM, in which correlation analysis is applied to fluctuations in the fluorescence intensity.

A problem with existing FFM techniques is that, because measured quantities are very dependent on the optically defined observation volume, there tends to be a relatively large variation in the measurements of the same substance obtained during different acquisition series, or in different environments.

SUMMARY

It is an aim of at least some embodiments of the present disclosure to at least partially address one or more needs in the prior art.

According to one aspect, there is provided a method comprising: receiving, by a processing device, a first plurality of photon count values indicating a number of photons detected by an optical system during a plurality of first time periods as a result of laser beam excitation of an observation volume of a sample during fluorescence fluctuation microscopy analysis; calculating, by the processing device based on the first plurality of photon count values, a first count rate per molecule indicating the average number of photons detected per molecule of the observation volume; and generating, by the processing device based on the first count rate per molecule, a control signal for configuring a phase modulation device of the optical system.

According to one embodiment, the control signal is generated based on the first count rate per molecule and on at least one or more reference values.

According to one embodiment, the first plurality of photon count values indicate the number of photons detected while the phase modulation device is in a first configuration; and the one or more reference values comprise a second count rate per molecule based on a second plurality of photon count values indicating the number of photons detected during second time periods while the phase modulation device was in a second configuration different to the first configuration, and a third count rate per molecule based on a third plurality of photon count values indicating the number of photons detected during third time periods while the phase modulation device was in a third configuration different to the first and second configurations.

According to one embodiment, generating the control signal comprises calculating the control signal to maximize the count rate per molecule.

According to one embodiment, the first and second configurations are different degrees of at least one of the following optical effects: astigmatisms; comas; trefoils; primary spherical aberrations; and secondary spherical aberrations According to one embodiment, generating the first count rate per molecule comprises determining the average number of molecules in the observation volume based on the first count values.

According to one embodiment, the first count rate per molecule (CRM) is calculated based on the following equation: CRM=(<n>/δt)/<N>, where <N> is the average number of molecules in the observation volume, δt is the duration of each of the first time periods and <n> is the average of the first count values during the first time periods.

According to one embodiment, the reciprocal (1/<N>) of the number of molecules in the observation volume is determined based on the following equation:

$$\frac{1}{\langle N \rangle} = \frac{\langle \delta n_i \delta n_{i+1} \rangle}{\langle n \rangle^2}$$

where <n> is the average of the first count values, $\delta n_i$ is equal to $n_i - \langle n \rangle$, $n_i$ being the $i^{th}$ count value, and $\delta n_{i+1}$ is equal to $n_{i+1} - \langle n \rangle$, $n_{i+1}$ being the $(i+1)^{th}$ count value.

According to one embodiment, the reciprocal (1/<N>) of the number of molecules in the observation volume is determined based on the following equation:

$$\frac{1}{\langle N \rangle} = \frac{\langle n_i n_{i+1} \rangle}{\langle n \rangle^2} - 1$$

where <n> is the average of the first count values, $n_i$ and $n_{i+1}$ are the $i^{th}$ and $(i+1)^{th}$ count values.

According to one embodiment, the reciprocal (1/<N>) of the number of molecules in the observation volume is determined based on a temporal autocorrelation function.

According to one embodiment, the method further comprises performing fluorescence microscopy analysis of the sample while the phase modulation device is configured by the control signal to at least partially correct optical aberrations.

According to a further aspect, there is provided a non-transitory storage device storing a computer program configured, when executed by a processing device, to implement the above method.

According to a further aspect, there is provided a processing device configured to: receive photon count values for a plurality of time periods indicating a number of photons detected by an optical system as a result of laser beam excitation of an observation volume of a sample during fluorescence fluctuation microscopy analysis; calculate, based on the photon count values, a count rate per molecule, indicating the average number of photons detected per molecule of the observation volume; and generate, based on the determined count rate per molecule, a control signal for controlling a phase modulation device of the optical system.

According to a further aspect, there is provided an adaptive optics system comprising: a phase modulation device; and the above processing device.

According to yet a further aspect, there is provided a fluorescence fluctuation microscopy analysis system comprising: the above adaptive optics device; and a photon detector.

According to one embodiment, the phase modulation device is a deformable mirror or a spatial light modulator.

BRIEF DESCRIPTION OF THE DRAWINGS

The foregoing and other features and advantages will become apparent from the following detailed description of embodiments, given by way of illustration and not limitation with reference to the accompanying drawings, in which:

FIG. 1 illustrates a fluorescence fluctuation microscopy (FFM) analysis system according to an embodiment of the present disclosure;

FIG. 2 illustrates examples of a laser beam focused at different depths in a sample;

FIG. 3 represents an observation volume within a sample according to an example embodiment;

FIG. 4A is a flow diagram showing operations in a method according to an embodiment of the present disclosure;

FIG. 4B is a graph showing examples of count rates per molecule measured based on different degrees of an optical effect;

FIGS. 5A and 5B illustrate a phase modulation device according to an example embodiment of the present disclosure;

FIG. 6 illustrates a phase modulation device according to a further example embodiment of the present disclosure; and FIG. 7 illustrates a control unit according to an example embodiment of the present disclosure.

DETAILED DESCRIPTION

FIG. 1 illustrates a fluorescence microscopy analysis system 100 for performing fluorescence microscopy according to an example embodiment of the present disclosure.

A sample 102, which is for example an organic or inorganic substance, optionally supported on a slide (not illustrated), is positioned at one end of an optical arrangement 103. A laser source 104 is provided at another end of the optical arrangement 103 and generates a laser beam, which is for example supplied to the sample via a monomode optical fiber 106 and other optical elements of the optical arrangement 103 described in more detail below. A fluorescence detector 108, which is for example an avalanche photodiode, receives the fluorescent signal returned from the sample via the other optical elements of the optical arrangement 103 and via an optical fiber 110.

An example of the optical elements of the optical arrangement 103 linking the sample 102, the laser source 104 and fluorescence detector 108, is represented in FIG. 1, and will now be described in more detail. It will be apparent to those skilled in the art that such an arrangement represents an example only, and that there are numerous modifications and alternatives that could be applied to this optical arrangement.

In FIG. 1, solid lines 112 and 113 represent the edge limits of an optical path between the laser source 104, the sample 102, and the fluorescence detector 108. A dashed-dotted line 114 represents the center of the optical path.

As illustrated, the laser beam provided by the laser source 104 via the monomode optical fiber 106 for example diverges and passes though a converging lens element 116, which modifies the diverging beam into a parallel beam provided to a dichroic mirror 118. The dichroic mirror 118 diverts the laser beam towards a phase modulation device 120, via further converging lens elements 122 and 124. As will be described in more detail below, the phase modulation device 120 is for example a deformable mirror or a spatial light modulator. The converging lens element 122 for example creates a focal point 123 between the lens elements 122 and 124, and the converging element 124 for example modifies the light into a parallel beam wider than the beam falling on the lens element 122, and for example having a width adapted to the active area of the phase modulation device 120.

The light beam reflected from the phase modulation device 120 is provided to a converging lens element 126, which focuses the beam to a focal point 127. In some embodiments, during a calibration phase of the optical arrangement 100, a beam splitter 128 is positioned between the lens element 126 and the focal point 127, and diverts part of the beam to a phase sensor 129, via a further converging lens element 130. The phase sensor 129 is for example a Shack-Hartmann phase sensor. During the calibration phase, the effects of various deformations applied by the phase modulation device 120 are for example tested by the phase sensor 129, permitting such deformations to be quantified.

After the focal point 127, the light beam for example diverges towards a converging lens element 132, which modifies the beam into a parallel beam provided, via a mirror 134 and/or an XY scanner 136, towards the sample 102. XY scanner 136 permits an image to be generated based on the fluorescence signal from a certain zone of the sample. In particular, the XY scanner for example directs the laser beam to various positions in the XY plan of the sample, under the control of a control signal generated by a control device (not illustrated in FIG. 1).

In the example of FIG. 1, further converging lens elements 138 and 140, and a lens objective 142 are for example provided between the XY scanner 136 and the sample 102. The lens element 138 for example focuses the light beam to a focal point 143 between the lens elements 138 and 140. The lens element 140 for example modifies the diverging light beam into a parallel beam, which is provided to the lens objective 142. The lens objective 142 focuses the light beam to a focal point within the sample 102.

After fluorescence excitation of molecules within an observation volume in the sample 102, fluorescent light, which is for example at a wavelength different from that of the laser beam, is returned along a same light path as the laser beam. In particular, the return light is passed through the lens objective 142, the lens element 140 and 138, the XY scanner 136 and mirror element 134 if present, the lens elements 132 and 126, the phase modulation device 120, and the lens elements 122 and 120. However, rather than being reflected by the dichroic mirror 118 towards the laser source, the fluorescent light, being at a different wavelength to the laser beam, passes through the dichroic mirror 118 and continues to a further lens element 144, which focuses the fluorescent light beam onto the end of the optical fiber 110 leading to the fluorescence detector 108.

In some embodiments, the optical fiber 110 is provided to ensure a focusing of the optical system on a particular volume of the sample. This optical fiber 110 plays the role of a pin-hole and could be replaced by a pin-hole in alternative embodiments. Alternatively, instead of one-photon excitation, a two-photon excitation system may be implemented, in which two photons of the laser beam are required to excite each molecule. In such a case, the optical fiber 110 or pinhole is for example no longer present. The signal from the detector 108 is for example provided to a counter 146, which counts the number of detected photons. In particular, the fluorescence detector 108 for example generates a pulse each time a photon is detected and the counter 146 counts these pulses during a number of sampling periods in order to determine the number of photons received during the sampling periods.

Based on the count values generated by the counter 146, a control unit 148 determines measures regarding the sample, such as the count rate per molecule within the observation volume. According to the embodiments described herein, the count rate per molecule provides a metric, in other words a basis, for evaluating the extent of the optical aberrations present in the system. In particular, in order to reduce aberrations, the control signal is chosen to maximize the count rate per molecule. The phase modulation device 120 is controlled by the control unit 148 based on the measured count rate per molecule, in order to converge towards an aberration free optical system, as will be described in more detail below.

FIG. 2 illustrates the convergence of the laser beam into the sample 102 of FIG. 1, and shows examples of different penetration depths during two different measurements of a same substance. In particular, during a first measurement, the laser beam, shown by solid lines 201, for example penetrates into the sample 102 and converges to a focal point at a depth $d_1$ from the surface of the sample. This leads to an observation volume corresponding to a zone labeled 202 around the focal point. During a second measurement, the laser beam, shown by dashed lines 203, for example penetrates into the sample 102 and converges to a focal point at a depth $d_2$ from the surface of the sample. In the example of FIG. 2, the depth $d_2$ is deeper than the depth $d_1$, for example due to a change in the optical arrangement or in the position of the sample 102.

The present inventors have observed that such a difference in the depths $d_1$ and $d_2$ of different measurements can lead to a relatively large difference in the readings for each measurement, while the readings should remain substantially constant irrespective of the depth. This difference can be attributed at least in part to a variation in the optical aberrations present during each of the measurements caused by the varying depths.

FIG. 3 schematically represents an example of an observation volume 302. As illustrated, a region of the sample represented by a circle 300 comprises molecules labeled 301. A volume 302 within the region 300 that is excited by the laser beam is shown non-shaded in FIG. 3, and has the typical waist form resulting from the focusing of the laser beam. The molecules 301 falling within a zone 304 of the region 300, shown shaded in FIG. 3, surrounding the volume 302, are not excited by the laser beam.

Within the volume 302, an observation volume 306 has the form of an ellipsoid in which not only are the molecules excited, but the resulting fluorescence is observed by the optical system. The observation volume is for example defined by the optical fiber 110, or a pin-hole, of the optical system, or by the wavelength of the laser beam in the case of two-photon excitation configuration. As known in the art, two-photon excitation involves doubling the wavelength of the laser beam light, thereby halving the excitation energy of each photon such that rather than a single photon being sufficient to excite the fluorescence of each molecule, two photons are required. The only volume in which the intensity of light is high enough for there to result in two photons hitting the same molecule during a sub-picosecond time period corresponds to the observation volume 306.

The observation volume 306 is represented as having a width of $2\,W_r$, where $W_r$ is the radial waist of the observation volume, and a height of $2\,W_z$, where $W_z$ is the axial waist of the observation volume in the direction of the laser beam. The radial waist $W_r$ of the observation volume may not be the same in the x and y directions, in which case two different radial widths $W_x$ and $W_y$ could be used to define the observation volume.

FIG. 4 is a flow diagram illustrating operations in a method of correcting aberrations in fluorescent microscopy optical system according to an example embodiment.

In an operation 402, count values $n_1$ to $n_I$ are received corresponding to a plurality I of respective time periods $t_1$ to $t_I$. In particular, during analysis of a sample, photons are counted by the photon counter 146 of FIG. 1 for I time periods $t_1, t_2 \ldots t_I$, to provide the corresponding count values $n_1$ to $n_I$. The time periods are for example successive time periods, although in alternative embodiments there could be a time interval between some or all of the time periods. In one example, each time period is between 1 and 30 microseconds, for example around 10 microseconds. Furthermore, in one example, the overall count duration for all time periods is between 1 and 10 seconds, for example in the region of 2 seconds. In alternative embodiments, the photon count could be obtained by recording the time intervals between the arrivals of the successive photons.

In another operation 404, the count rate per molecule (CRM) is determined based on the count values, as will now be described in more detail.

The count rate per molecule, for example expressed as Hz per molecule and sometimes referred to as the brightness, in an observation volume of a sample, can be defined as $(\langle n\rangle/\delta t)/\langle N\rangle$, where n is the count value, $\delta t$ is the time period, N is the number of molecules in the observation volume, and $\langle\cdot\rangle$ denotes a temporal averaging. The reciprocal of the mean number of molecules $1/\langle N\rangle$ in the observation volume can be determined based on the following equation:

$$\frac{1}{\langle N\rangle} = \frac{\langle \delta n_i \delta n_{i+1}\rangle}{\langle n\rangle^2}$$

where $\delta n_i$ is equal to $n_i-\langle n\rangle$, $n_i$ being the $i^{th}$ count value, and $\delta n_{i+1}$ is equal to $n_{i+1}-\langle n\rangle$, $n_{i+1}$ being the $(i+1)^{th}$ count value. The equation is for example applied to all of the count values $n_1$ to $n_{(I-1)}$. Once the value $1/\langle N\rangle$ has been determined, the CRM can be determined by multiplying this value by the mean count value $\langle n\rangle$ and dividing it by the time period $\delta t$.

In an alternative embodiment, the reciprocal of the mean number of molecules $1/\langle N\rangle$ in the observation volume can be determined based on the following equation:

$$\frac{1}{\langle N\rangle} = \frac{\langle n_i n_{i+1}\rangle}{\langle n\rangle^2} - 1$$

where, as before, $n_i$ and $n_{i+1}$ are the $i^{th}$ and $(i+1)^{th}$ count values. Again, once the value $1/\langle N \rangle$ has been determined, the CRM can be determined by multiplying this value by the mean count value $\langle n \rangle$ and dividing it by the time period $\delta t$.

Alternatively, the reciprocal of the mean number of molecules $1/\langle N \rangle$ in the observation volume can be determined based on the following equation:

$$\frac{1}{\langle N \rangle} = \frac{\langle \delta^2 n \rangle - \langle n \rangle}{\langle n \rangle^2}$$

where $\delta^2 n$ is the variance of the count values. Again, once the value $1/\langle N \rangle$ has been determined, the CRM can be determined by multiplying this value by the mean count value $\langle n \rangle$ and dividing it by the time period $\delta t$.

Alternatively, the temporal autocorrelation function $G(\tau)$ can be used to determine the reciprocal of the mean number of molecules $1/\langle N \rangle$ in the observation volume, for example based on the following equation:

$$G(\tau_j) = \frac{\langle n_i n_{i+j} \rangle}{\langle n \rangle^2} = 1 + \frac{\langle \delta n_i \delta n_{i+j} \rangle}{\langle n \rangle^2} = 1 + \frac{1}{\langle N \rangle} g(\tau_j)$$

Thus the value of $1/\langle N \rangle$, and the parameters describing the function $g(\tau_j)$ can be determined by fitting $G(\tau_j)$. Knowing that $g(0^+)=1$, the value of $1/\langle N \rangle$ can be determined from the behavior of $G(\tau_j)$ when $\tau_j \to 0$, without requiring an exhaustive mathematical description of the global shape of $G(\tau_j)$.

Thus there are a number of different methods that may be used to determine the count rate per molecule based on the measured count values $n_1$ to $n_J$. Furthermore, the above methods are merely examples, there being alternative methods that could be used in some embodiments.

Referring again to FIG. 4A, a further operation 406, a control signal is generated, based on the determined count rate per molecule, for controlling the phase modulation device 120 of the optical arrangement of FIG. 1. For example, the control signal is chosen to maximize the count rate per molecule.

In one example, the control unit 148 compares the count rate per molecule to one or more reference values in order to determine the control signal to be provided to the phase modulation device. The reference values are for example count rates per molecule previously determined for different configurations of the phase modulation device, as will now be described with reference to FIG. 4B.

FIG. 4B is a graph representing an example of an operation performed by the control unit 148 in order to determine an improved configuration of the phase modulation device based on the measured value of the count rate per molecule, to reduce optical aberrations. For example, CRM values are determined for three configurations $-\alpha$, 0 and $\alpha$ of the phase modulation device, where 0 corresponds to zero phase modulation, and $-\alpha$ and $\alpha$ correspond to negative and positive degrees of a certain optical effect, referred to herein as a Zernike mode. In the embodiments described herein, the following eight Zernike modes will be considered: the two forms of astigmatism; the two forms of coma; the two forms of trefoil; primary spherical aberrations; and secondary spherical aberrations. It will be apparent to those skilled in the art that fewer Zernike modes or additional Zernike modes could be considered.

The method for example involves measuring in turn the CRM values for three configurations $-\alpha$, 0 and $\alpha$ of the phase modulation device. Then, a curve 410 is estimated that passes through the three CRM values, and the position of the peak of this curve is determined, for example by differentiation. An optimal configuration of the phase modulation device can then be estimated for this Zernike mode.

In the example of FIG. 4B, the optimal configuration of the Zernike mode is at approximately $-\alpha/2$.

The process described with respect to FIG. 4B is for example repeated for each Zernike mode to be considered, and once estimations for optimal configurations of the phase modulation device for each Zernike mode have been calculated, the phase modulation device 120 is for example controlled based on a summation of all of the estimated optimal configurations of each Zernike mode. In embodiments, a second open loop may be performed to further improve the mode optimization.

The phase modulation device 120 may be implemented by any of a number of different devices, two examples of which will now be described with reference to FIGS. 5A, 5B and 6.

FIG. 5A illustrates a deformable mirror 500 implementing the phase modulation device according to one example embodiment. The deformable mirror 500 comprises a deformable membrane 502, which has an outer surface that is reflective to light. A series of magnets 504 are positioned at regular intervals across its under surface, and a solenoid 506 is positioned facing each magnet 504 on support 508, each solenoid being aligned with its corresponding magnet. For ease of illustration, only a single line of magnets and corresponding solenoids is illustrated in FIG. 5A, but of course the membrane 502 is a 2-dimensional surface, with a 2-dimensional array of magnets positioned across its underside.

By passing a certain current through each solenoid, the magnets 504 can each be moved to a position closer to or further from the support 508, thereby permitting the membrane to be configured in many different configurations.

FIG. 5A illustrates the deformable mirror 500 in a neutral state in which the membrane 502 is flat.

FIG. 5B illustrates the deformable mirror 500 in an example in which currents are applied to each solenoid such that the membrane 502 is configured to adopt an irregular shape.

FIG. 6 illustrates a spatial light modulator 600 according to an alternative implementation of the phase modulation device 120 of FIG. 1. The spatial light modulator 600 comprises a layer 602 of a birefringent liquid crystal material having a configurable refractive index, and an inner reflective surface 603. In particular, a number of electrodes 604 are provided at regular intervals close to the underside of layer 602 in order to generate electrical fields in corresponding portions of the layer 602. For ease of illustration, only a single line of electrodes 604 is represented in FIG. 6, but of course the layer 602 has a 2-dimensional surface receiving light waves, and a 2-dimensioanl array of electrodes will be positioned across the underside of layer 602.

The refractive index of the material in the regions overlying each electrode 604 is dependent on the strength of the corresponding electrical field, and the electrical fields can be varied by applying different voltages to each electrode 604. The effect, as represented in FIG. 6 by light waves 608 and 610, is to vary the speed that light passes through the layer 602 to its reflective internal surface 603, and is reflected back through the layer 602. Light wave 608 passes relatively quickly through one region of the layer 602, whereas light wave 610 takes longer to pass through the layer 602 in another region. The result of the variable speed of the light rays is that a variable phase variation can be applied across the device, leading to a variable phase modulation, assuming that the incident light is appropriately polarized.

FIG. 7 illustrates the control unit 148 of FIG. 1 in more detail according to an example embodiment of the present disclosure. The control unit 148 is for example configured to implement the operations 402, 404 and 406 described above in relation to FIG. 4A.

Control unit 148 for example comprises a processing device 702 under the control of an instruction memory 704. By way of example, instruction memory 704 may include one or more non-transitory computer readable storage media, including by way of example hard drives or other magnetic media, optical media and flash drives and other flash memory storage devices, having stored thereon computer program code and/or instructions which, when accessed and executed by a processing device, cause the processing device to perform any of the steps described in the present application as performed by any processing device, including control unit 148. A data storage device or memory 706 is also coupled to the processing device 702, and for example stores the photon counts generated by the photon counter 146 of FIG. 1. An input/output device or module 708 for example receives the count values from the photon counter 146, and also provides a control signal to the phase modulation device 120. A user interface 710 is for example provided, allowing an operator to configure certain parameters, such as the number and types of Zernike modes to be tested, etc.

Thus, in the present description, the use of an optics system has been proposed for improving the reliability of FFM techniques, and in particular for increasing the signal to noise ratio in the FFM experiment. The rate of photon arrival emitted per fluorescent molecule, stated in another way the count rate per molecule CRM, is measured in real time. CRM measurements are advantageously insensitive to non-cryptic photo-bleaching, and can be used to correct aberrations in an efficient and effective manner.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A method comprising:
    performing fluorescence fluctuation microscopy analysis by laser beam excitation of an observable volume of a sample using an optical system comprising a phase modulation device and a photon detector;
    receiving, by a processing device, a first plurality of photon count values indicating a number of photons detected by the optical system during a plurality of first time periods;
    calculating, by the processing device based on said first plurality of photon count values, a first count rate per molecule indicating the average number of photons detected per molecule of the observation volume;
    generating, by the processing device based on the first count rate per molecule, a control signal; and
    reducing optical aberrations by configuring the phase modulation device of said optical system using the control signal.

2. The method of claim 1, wherein said control signal is generated based on said first count rate per molecule and on at least one or more reference values.

3. The method of claim 2, wherein:
    said first plurality of photon count values indicate the number of photons detected while said phase modulation device is in a first configuration; and
    said one or more reference values comprise a second count rate per molecule based on a second plurality of photon count values indicating the number of photons detected during second time periods while said phase modulation device was in a second configuration different to said first configuration, and a third count rate per molecule based on a third plurality of photon count values indicating the number of photons detected during third time periods while said phase modulation device was in a third configuration different to said first and second configurations.

4. The method of claim 1, wherein generating said control signal comprises calculating said control signal to maximize the count rate per molecule.

5. The method of claim 3, wherein said first and second configurations are different degrees of at least one of the following optical effects:
    astigmatisms;
    comas;
    trefoils;
    primary spherical aberrations; and
    secondary spherical aberrations.

6. The method of claim 1, wherein generating said first count rate per molecule comprises determining the average number of molecules in said observation volume based on said first count values.

7. The method of claim 6, wherein said first count rate per molecule (CRM) is calculated based on the following equation:

$$CRM = (\langle n \rangle / \delta t) / \langle N \rangle$$

where $\langle N \rangle$ is the average number of molecules in the observation volume, $\delta t$ is the duration of each of said first time periods and $\langle n \rangle$ is the average of said first count values during said first time periods.

8. The method of claim 7, wherein the reciprocal ($1/\langle N \rangle$) of the number of molecules in the observation volume is determined based on the following equation:

$$\frac{1}{\langle N \rangle} = \frac{\langle \delta n_i \delta n_{i+1} \rangle}{\langle n \rangle^2}$$

where $\langle n \rangle$ is the average of the first count values, $\delta n_i$ is equal to $n_i - \langle n \rangle$, $n_i$ being the ith count value, and $\delta n_{i+1}$ is equal to $n_{i+1} - \langle n \rangle$, $n_{i+1}$ being the (i+1)th count value.

9. The method of claim 7, wherein the reciprocal ($1/\langle N \rangle$) of the number of molecules in the observation volume is determined based on the following equation:

$$\frac{1}{\langle N \rangle} = \frac{\langle n_i n_{i+1} \rangle}{\langle n \rangle^2} - 1$$

where $\langle n \rangle$ is the average of the first count values, $n_i$ and $n_{i+1}$ are the ith and (i+1)th count values.

10. The method of claim 7, wherein the reciprocal (1/<N>) of the number of molecules in the observation volume is determined based on a temporal autocorrelation function.

11. The method of claim 1, further comprising performing fluorescence microscopy analysis of said sample while said phase modulation device is configured by said control signal to at least partially correct optical aberrations.

12. A fluorescence fluctuations microscopy analysis system, comprising:
an adaptive optics system configured to perform fluorescence fluctuation microscopy analysis by laser beam excitation of an observable volume of a sample comprising:
a phase modulation device;
a photon detector; and
a computer storage device storing a computer program, which when executed by a processing device, causes the processing device to:
receive a first plurality of photon count values indicating a number of photons detected by the photon detector during a plurality of first time periods;
calculate based on said first plurality of photon count values, a first count rate per molecule indicating the average number of photons detected per molecule of the observation volume; and
generate a control signal based on the first count rate per molecule to maximize the count rate per molecule and to configure the phase modulation device to reduce optical aberrations.

13. A fluorescence fluctuation microscopy analysis system comprising:
an adaptive optics system comprising:
a phase modulation device configured to reduce optical aberrations;
a processing device configured to:
receive photon count values for a plurality of time periods indicating a number of photons detected by the optical system as a result of laser beam excitation of an observation volume of a sample during fluorescence fluctuation microscopy analysis;
calculate, based on said photon count values, a count rate per molecule, indicating the average number of photons detected per molecule of the observation volume; and
generate, based on the determined count rate per molecule, a control signal for controlling the phase modulation device of said optical system; and
a photon detector.

14. The fluorescence microscopy analysis system of claim 13, wherein said phase modulation device is a deformable mirror.

* * * * *